US 9,788,869 B2

(12) United States Patent
Stad et al.

(10) Patent No.: US 9,788,869 B2
(45) Date of Patent: Oct. 17, 2017

(54) SPINAL FIXATION ELEMENT ROTATION INSTRUMENT

(75) Inventors: Shawn D. Stad, Fall River, MA (US);
Christopher L. Ramsay, West Wareham, MA (US); Thomas Gamache, Westport, MA (US);
Raymond F. Murphy, Attleboro, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 76 days.

(21) Appl. No.: 12/395,469

(22) Filed: Feb. 27, 2009

(65) Prior Publication Data
US 2010/0222828 A1 Sep. 2, 2010

(51) Int. Cl.
*A61B 17/70* (2006.01)
*A61B 17/88* (2006.01)

(52) U.S. Cl.
CPC ...... *A61B 17/7083* (2013.01); *A61B 17/8891* (2013.01); *A61B 17/701* (2013.01); *A61B 17/7011* (2013.01); *A61B 17/7085* (2013.01)

(58) Field of Classification Search
CPC ............ A61B 17/7083; A61B 17/7085; A61B 17/7091; A61B 17/7086; A61B 17/7088; A61B 17/7089
USPC .... 606/86 A, 86 R, 300, 246, 279; 81/121.1, 81/60–62, 29, 436, 440
See application file for complete search history.

(56) References Cited

U.S. PATENT DOCUMENTS

| 755,569 | A | * | 3/1904 | Freeland | 81/61 |
| 3,726,161 | A | * | 4/1973 | Williams et al. | 81/60 |
| 4,016,782 | A | * | 4/1977 | Guimarin | 81/63 |
| 4,507,990 | A | * | 4/1985 | Lack | 81/57.39 |

(Continued)

FOREIGN PATENT DOCUMENTS

| CN | 1972637 A | 5/2007 |
| CN | 102413776 A | 4/2012 |

(Continued)

OTHER PUBLICATIONS

International Search Report and Written Opinion for Application No. PCT/US2010/025643, dated Apr. 23, 2010.

(Continued)

*Primary Examiner* — Jan Christopher Merene
*Assistant Examiner* — Atiya Mahmud
(74) *Attorney, Agent, or Firm* — Nelson Mullins Riley & Scarborough LLP

(57) ABSTRACT

A spinal fixation element rotation instrument with two lever arms is provided. The lever arms are connected to each other at distal ends thereof. The second lever arm rotates relative to the first lever arm. The distal ends of the first and second lever arms are adapted to couple to a spinal fixation element. The distal ends of the lever arms may have a dual ratchet feature that prevents rotation in a set direction. When one arm rotates back and forth, the other arm is held stationary. As a result, the spinal fixation element rotates in a predetermined direction and is prevented from rotating back toward its initial position. The direction of the rotation of the spinal fixation element may be set using knobs or switches provided at a proximal end of one or both of the lever arms.

9 Claims, 19 Drawing Sheets

(56) References Cited

U.S. PATENT DOCUMENTS

| | | | | |
|---|---|---|---|---|
| 5,207,130 | A * | 5/1993 | Payne | B25B 13/44 |
| | | | | 279/50 |
| 5,329,834 | A | 7/1994 | Wong | |
| 5,740,704 | A * | 4/1998 | Payne | B25B 13/44 |
| | | | | 279/50 |
| 5,740,706 | A * | 4/1998 | Tseng | 81/490 |
| 6,295,895 | B1 * | 10/2001 | Hejninger | 81/57.39 |
| 7,104,165 | B2 * | 9/2006 | Chu | 81/177.8 |
| 7,219,581 | B2 * | 5/2007 | Tulloch et al. | 81/112 |
| 7,246,540 | B2 * | 7/2007 | Rillera | B25B 9/00 |
| | | | | 294/100 |
| 7,491,207 | B2 | 2/2009 | Keyer et al. | |
| 7,707,916 | B2 * | 5/2010 | Pirseyedi | B25B 13/44 |
| | | | | 279/64 |
| 7,878,092 | B1 * | 2/2011 | Eby | B25B 7/02 |
| | | | | 81/112 |
| 2003/0208203 | A1 | 11/2003 | Lim et al. | |
| 2005/0038432 | A1 | 2/2005 | Shaolian et al. | |
| 2006/0196317 | A1 * | 9/2006 | Kinskey | 81/63.1 |
| 2007/0276406 | A1 * | 11/2007 | Mahoney et al. | 606/106 |
| 2007/0282337 | A1 * | 12/2007 | Garamszegi | A61B 17/7086 |
| | | | | 606/53 |
| 2008/0243190 | A1 | 10/2008 | Dziedzic et al. | |
| 2008/0255563 | A1 | 10/2008 | Farr et al. | |
| 2008/0312703 | A1 | 12/2008 | Hestad et al. | |

FOREIGN PATENT DOCUMENTS

| | | |
|---|---|---|
| JP | 2005-169064 | 6/2005 |
| JP | 5599829 B2 | 10/2014 |
| WO | 2010/099478 A1 | 9/2010 |

OTHER PUBLICATIONS

Chinese Office Action for Application No. 201080019287.2, 27 pages, dated Jul. 31, 2013.
Chinese Office Action for Application No. 201080019287.2, 17 pages, dated Mar. 27, 2014.
European Office Action for Application No. 10746936.3, 7 pages, dated Nov. 5, 2013.
Japanese Office Action for Application No. 2011-552198, 4 pages, dated Dec. 17, 2013.
Australian Office Action for Application No. 2010217838, 3 pages, dated Apr. 23, 2015.
Chinese Office Action for Application No. 201080019287.2, 5 pages, dated Oct. 8, 2014.
International Preliminary report on Patentability, PCT Application No. PCT/US2010/025643, dated Aug. 30, 2011, 8 pages.
Australian Office Action for Application No. 2010217838, 3 pages, dated May 29, 2014.
Australian Patent Examination Report for Application No. 2016201287, 2 pages, dated Sep. 21, 2016.

* cited by examiner

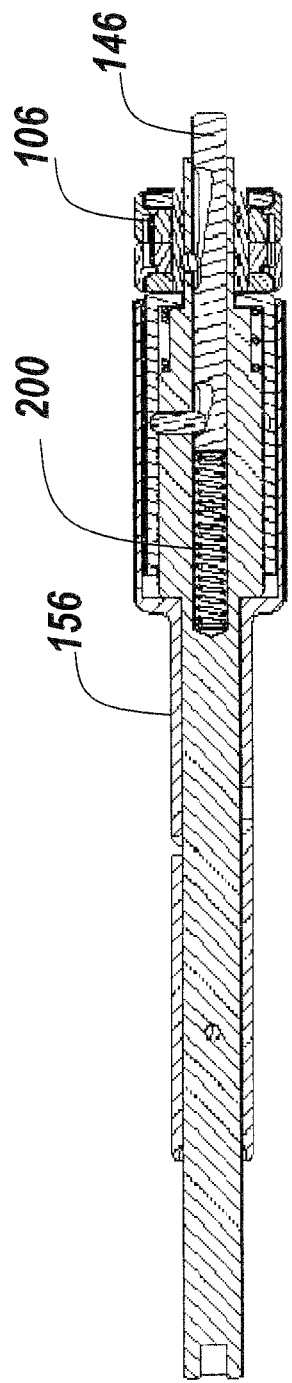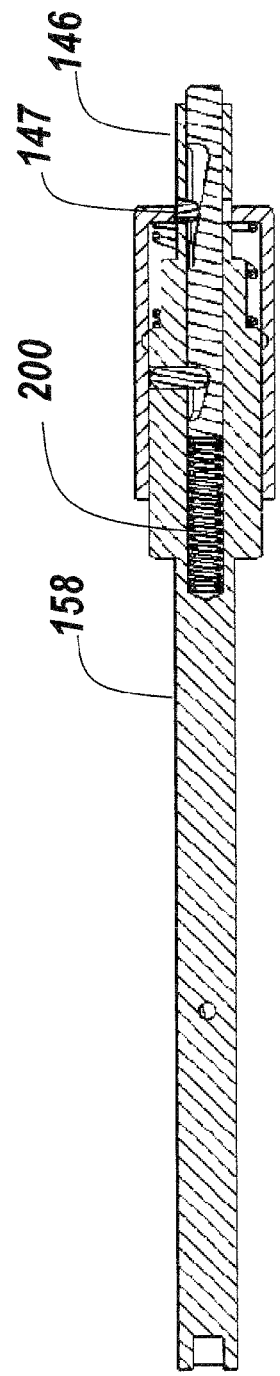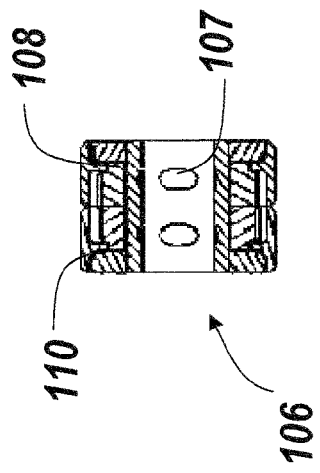
FIG. 2A
FIG. 2B
FIG. 2C

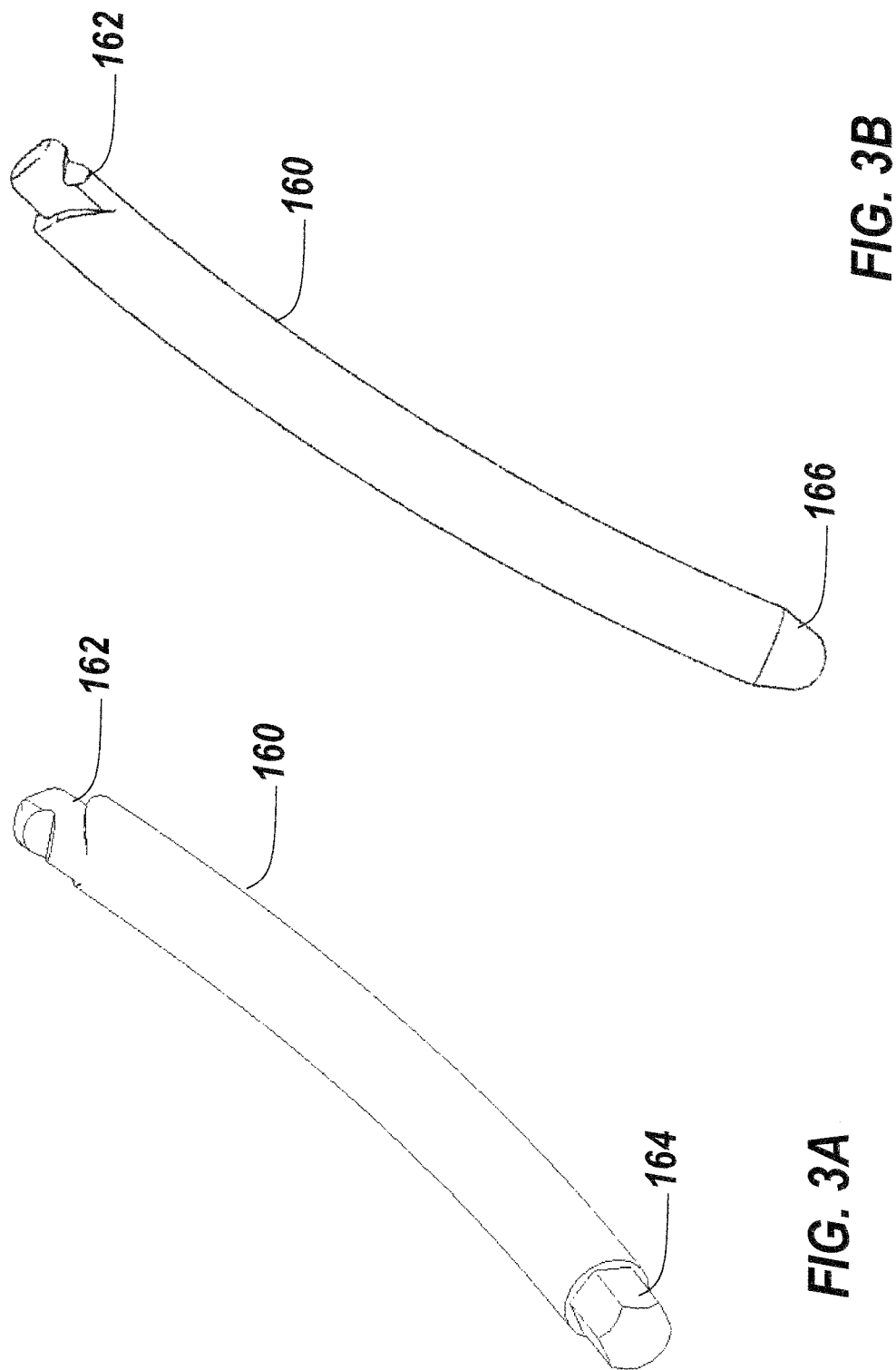

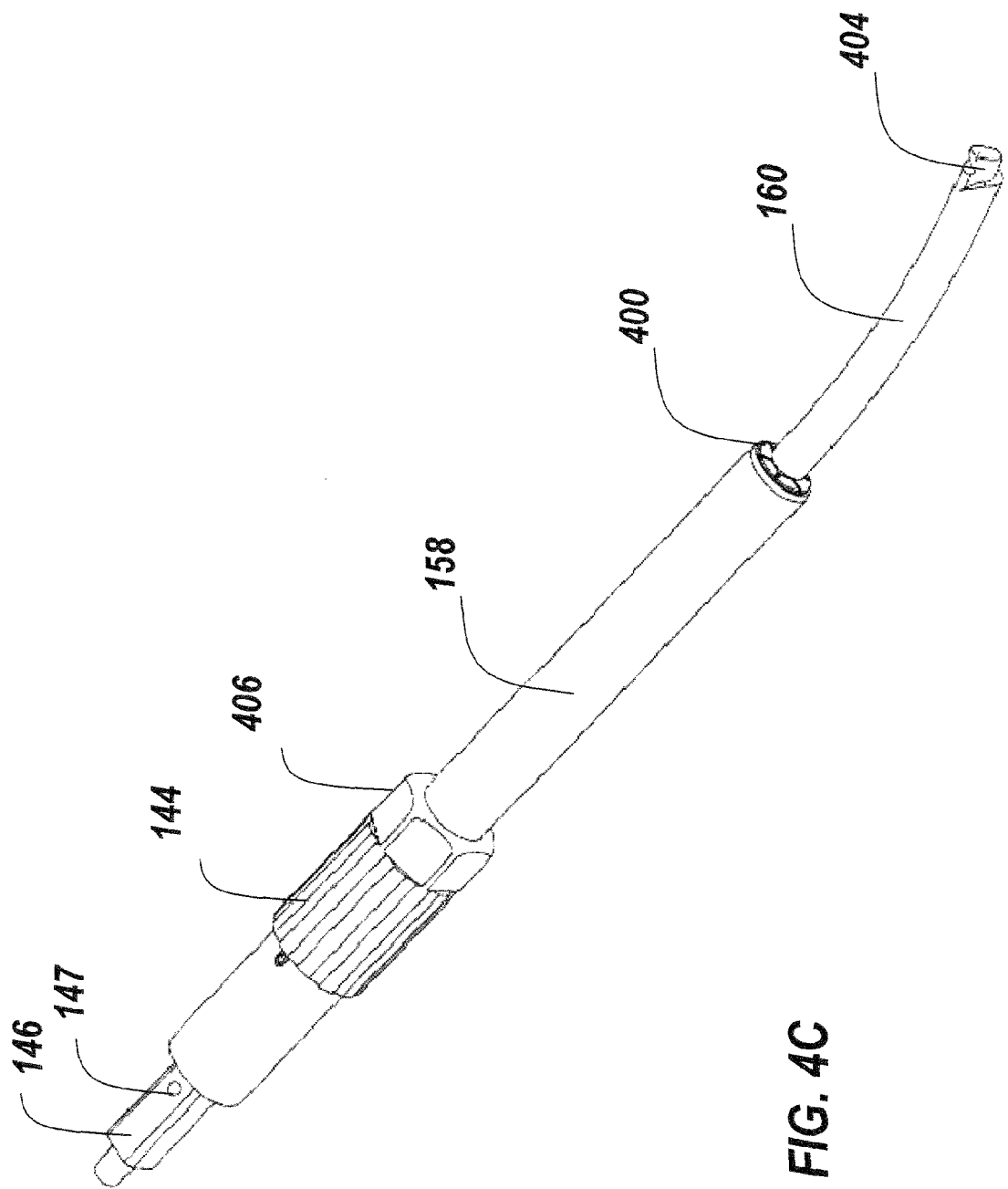

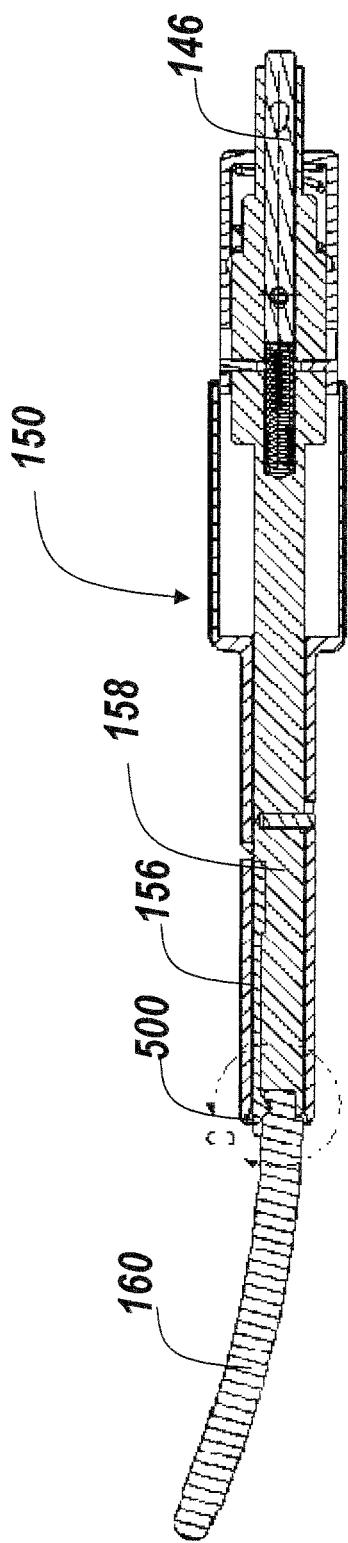
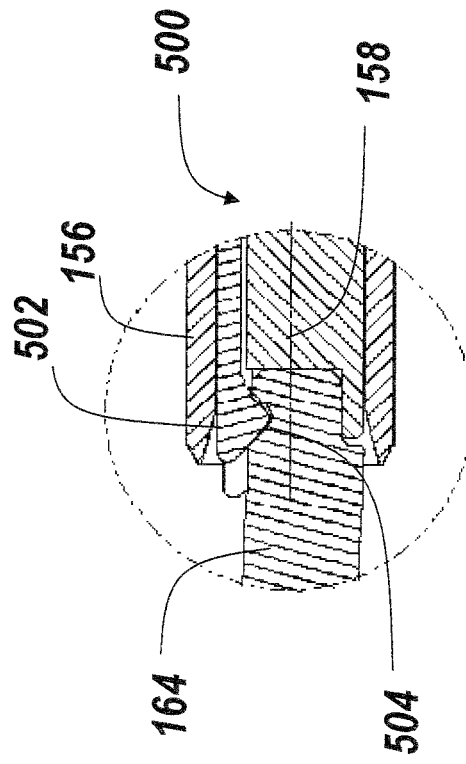
FIG. 5A
FIG. 5B

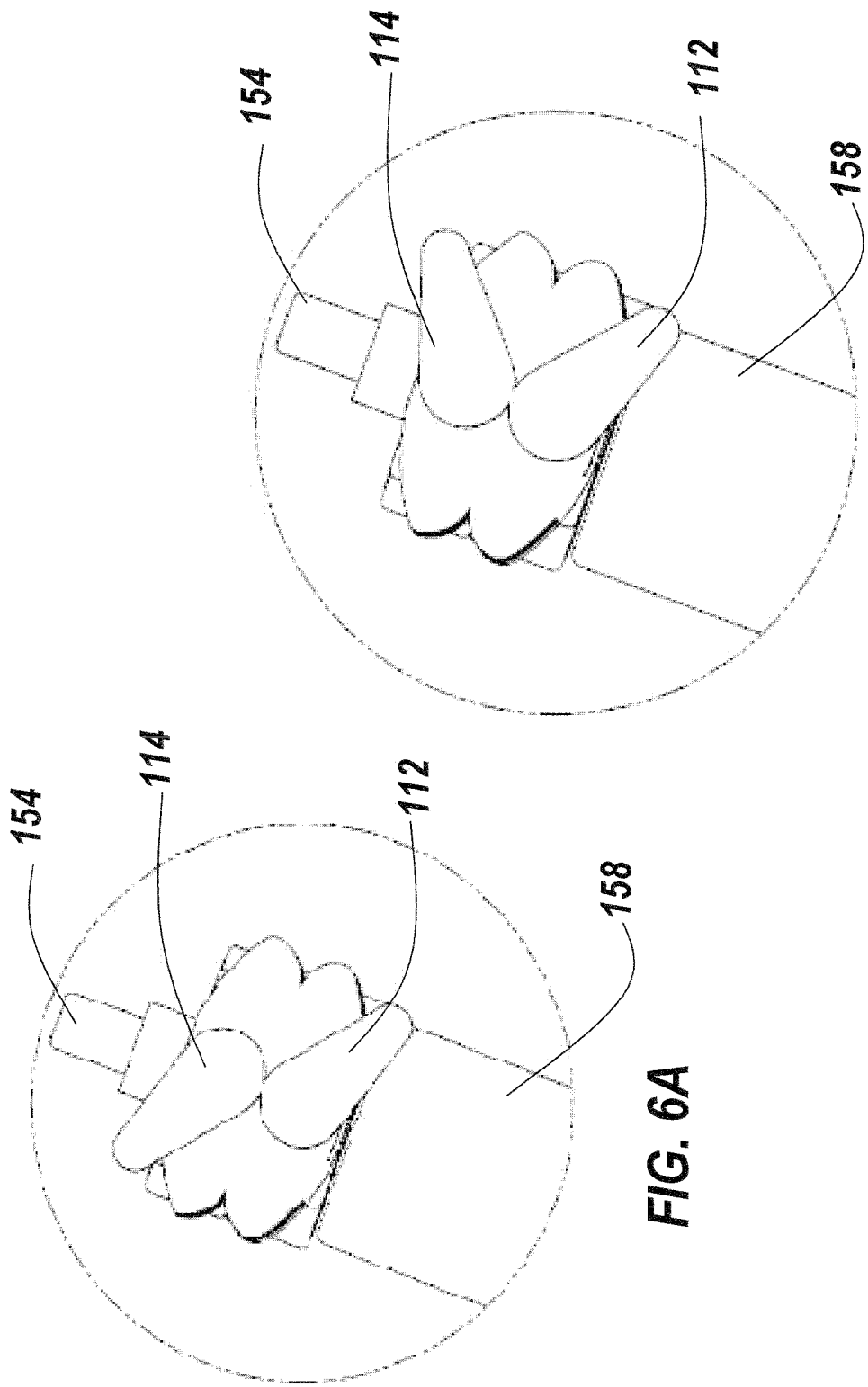

950

```
┌─────────────────────────────────────────────────────────────┐
│ Set the first ratchet and the second ratchet to rotate     │
│ clockwise                                                   │
│ 952                                                         │
└─────────────────────────────────────────────────────────────┘
                              │
                              ▼
┌─────────────────────────────────────────────────────────────┐
│ Couple the spinal fixation element rotation instrument to   │
│ the extension element 954                                   │
└─────────────────────────────────────────────────────────────┘
                              │
                              ▼
┌─────────────────────────────────────────────────────────────┐
│ Couple the extension element to the spinal fixation element │
│ 956                                                         │
└─────────────────────────────────────────────────────────────┘
                              │
                              ▼
┌─────────────────────────────────────────────────────────────┐
│ Insert the spinal fixation element and a portion of the     │
│ extension element through a skin incision 958               │
└─────────────────────────────────────────────────────────────┘
                              │
                              ▼
┌─────────────────────────────────────────────────────────────┐
│ Place the spinal fixation element through a bone anchor     │
│ opening 960                                                 │
└─────────────────────────────────────────────────────────────┘
                              │
                              ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ Rotate the spinal fixation element under the skin by        │
│ rotating the second ratchet 962                             │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                              │
                              ▼
                            ( A )
```

FIG. 11A

SPINAL FIXATION ELEMENT ROTATION INSTRUMENT

FIELD OF THE INVENTION

The present invention relates to spinal connection devices used in orthopedic surgery. More particularly, the present invention may relate to a spinal fixation element rotation instrument with dual lever arms that couple to and rotate a spinal fixation element when positioning the spinal fixation element through bone anchors placed on vertebrae.

BACKGROUND OF THE INVENTION

Spinal fixation systems may be used in surgery to align, adjust and/or fix portions of the spinal column, i.e., vertebrae, in a desired spatial relationship relative to each other. Many spinal fixation systems employ a spinal fixation element, e.g. a spinal fixation rod, for supporting the spine and for properly positioning components of the spine for various treatment purposes. Vertebral bone anchors, comprising pins, bolts, screws, and hooks, engage the vertebrae and connect the supporting spinal fixation element to different vertebrae. The size, length and shape of the spinal fixation element depend on the size, number and position of the vertebrae to be held in a desired spatial relationship relative to each other by the apparatus.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a spinal fixation element-receiving portion for receiving a spinal fixation element. A set-screw, plug, cap or similar type of closure mechanism is used to lock the spinal fixation element into the spinal fixation element-receiving portion of the pedicle screw.

In conventional spinal surgery, first, anchoring devices are attached to vertebra, then a spinal rod is aligned with the anchoring devices and secured. For example, for conventional pedicle screw assemblies, first the engagement portion of each pedicle screw is threaded into a vertebra. Once the pedicle screw assembly is properly positioned, a spinal fixation rod is seated in the rod-receiving portion of each pedicle screw head. The rod is locked into place by tightening a cap or similar type of closure mechanism to securely interconnect each pedicle screw to the fixation rod. This type of conventional spinal surgical technique usually involves making a surgical access opening in the back of the patient. Because exact placement of the screw assemblies depends on a patient's particular bone structure and bone quality, the exact position of all screw assemblies cannot be known until after all the assemblies are positioned. Adjustments, such as bending, are made to the spinal rod to ensure that it aligns with each screw assembly.

When placing the spinal fixation element in a long construct, the spinal fixation element may be inserted in an inverted orientation to facilitate insertion and positioning of the spinal fixation element below fascia. Consequently, the spinal fixation element needs to be rotated prior to final positioning in order to match the curvature of the spine. The contemporary medical devices, such as spinal fixation element holders, do not accommodate the rotation of the spinal fixation element while performing a minimally invasive procedure. Rotating the spinal fixation element percutaneously typically requires an additional skin incision or increasing the size of the existing skin incision. Additionally, it is desirable to make minimal rotary adjustments for better control. Currently, surgeons have to select a long rod to provide a holding surface when the rod is placed through the skin incision. The extra portion of the rod is cut in situ, extending the surgery time and posing the risk of cutting the rod at an unintentional location.

The contemporary medical devices also require re-engagement of the device to the spinal fixation element multiple times and often a second instrument is required during the re-engagement to prevent the spinal fixation element from slipping back toward the initial position. Therefore, there is a need for an instrument that will accommodate the rotation of a spinal fixation element while preventing the spinal fixation element from rotating back toward the initial position following adjustment during a minimally invasive procedure.

SUMMARY

Embodiments of the present invention provide a spinal fixation element rotation instrument that allows controlled rotation of spinal fixation elements. The spinal fixation element rotation instrument may include two lever arms connected to each other at a distal end thereof. The first arm, i.e. the holder, is held stationary while the second arm, i.e. the driver, is configured to rotate in a predetermined direction relative to the first arm. The driver rotates the spinal fixation element within the bone anchors or the extensions thereof while the holder prevents the spinal fixation element from rotating back toward its initial position. The spinal fixation element rotation instrument rotates the spinal fixation element to steer the spinal fixation element through one or more bone anchors attached to vertebrae. The spinal fixation element rotation instrument may also force the bone anchors to move the vertebrae attached thereto to bring the spine into alignment.

According to a first aspect of the invention, an instrument for rotating a spinal fixation element is provided. The instrument includes a first lever arm and a second lever arm. A distal end of the first lever arm is adapted to couple to the spinal fixation element. The second lever arm is rotatably coupled to the first lever arm at the distal end thereof. A distal end of the second lever arm is adapted to couple to the spinal fixation element. The second lever arm rotates relative to the first lever arm, about a central axis of the distal ends of the first lever arm and the second lever arm to rotate the spinal fixation element from an initial position to a rotated position.

According to various aspects of the present invention, the first lever arm includes a first ratchet and the second lever arm includes a second ratchet forming a dual ratchet mechanism that prevents the spinal fixation element from rotating back toward the initial position. The instrument may further include an extension element. The extension element has a distal end adapted to couple to the spinal fixation element and a proximal end adapted to couple to the instrument. A portion of the extension element fits through a skin incision at a target site to guide the spinal fixation element under skin.

According to another aspect, the second lever arm may further include a first section, a second section and an attachment mechanism. The attachment mechanism attaches the first section to the second section so that the first section is rotatable relative to the second section about a central axis of the attachment mechanism. The central axis of the attachment mechanism is perpendicular to the central axis of the distal ends of the first lever arm and the second lever arm.

According to yet another aspect, the instrument may also include a first switch provided on a proximal end of the first lever arm. The first switch, when positioned at a first position, allows the first ratchet to rotate clockwise. The first switch, when positioned at a second position, allows the first ratchet to rotate counterclockwise. The instrument may also include a second switch provided on a proximal end of the second lever arm. The second switch, when positioned at a first position, allows the second ratchet to rotate clockwise. The second switch, when positioned at a second position, allows the second ratchet to rotate counterclockwise. The first ratchet and the second ratchet lock each other when the first switch is at the first position and the second switch is at the second position. At the locked out position, the first ratchet and the second ratchet prevent the spinal fixation element from rotating.

According to another aspect, a method for percutaneous positioning of a spinal fixation element through a plurality of bone anchors placed below fascia is provided. The plurality of bone anchors have an opening adapted to couple to the spinal fixation element. A proximal end of the spinal fixation element is coupled to a spinal fixation element rotation instrument including two lever arms connected to each other at a distal end of the spinal fixation element rotation instrument. The second lever arm rotates relative to a first lever arm about a central axis of the distal end of the spinal fixation element rotation instrument. A distal end of the spinal fixation element is inserted through an incision in proximity of a first bone anchor. The spinal fixation element is guided through the opening of the first bone anchor and a second bone anchor adjacent to the first bone anchor. The spinal fixation element is rotated within the distal end of the spinal fixation element rotation instrument using the spinal fixation element rotation instrument to accommodate the bone anchors.

According to another aspect of the present invention, a dual ratchet spinal fixation element rotation instrument holder is provided. The dual ratchet spinal fixation element rotation instrument includes a first ratchet and a second ratchet connected to the first ratchet at a distal end thereof. The first ratchet and the second ratchet are configured to couple to a spinal fixation element or to an extension element coupled to the spinal fixation element. One of the first ratchet or the second ratchet rotates the spinal fixation element in a first direction from an initial position to a rotated position. Other of the first ratchet or the second ratchet prevents the spinal fixation element from rotating back toward the initial position.

According to yet another aspect of the present invention, a method for positioning of a spinal fixation element through a plurality of bone anchors placed below fascia is provided. The plurality of bone anchors have an opening adapted to couple to the spinal fixation element. A proximal end of the spinal fixation element is coupled to a spinal fixation element rotation instrument having a lever arm. The spinal fixation element is placed through the opening of the first bone anchor. The spinal fixation element is guided though a second bone anchor. The lever arm is rotated in a first direction to effect rotation of the spinal fixation element about a central axis of the spinal fixation element in the first direction to a rotational position. The lever arm is rotated in a second direction, opposite the first direction, while maintaining the spinal fixation element in the rotational position.

BRIEF DESCRIPTION OF THE FIGURES

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

FIG. 2A illustrates a cross-sectional view of an exemplary extension element coupled to an exemplary spinal fixation element rotation instrument;

FIG. 2B illustrates a cross-sectional view of a carrier of the exemplary extension element illustrated in FIG. 2A;

FIG. 2C illustrates a cross-sectional view of the distal end of the exemplary spinal fixation element rotation instrument illustrated in FIG. 2A;

FIGS. 3A-3B illustrate exemplary spinal fixation elements according to various embodiments of the present invention;

FIGS. 4A-4C illustrate an exemplary coupling mechanism that couples the spinal fixation element to the extension element;

FIGS. 5A-5B illustrate another exemplary coupling mechanism that couples the spinal fixation element to the extension element;

FIGS. 6A-6B illustrate a first switch provided on the first lever arm and a second switch provided on the second lever arm;

FIGS. 11A-11B are a flow diagram of placing a spinal fixation element through a plurality of bone anchors.

DETAILED DESCRIPTION OF THE INVENTION

Figure 1A:
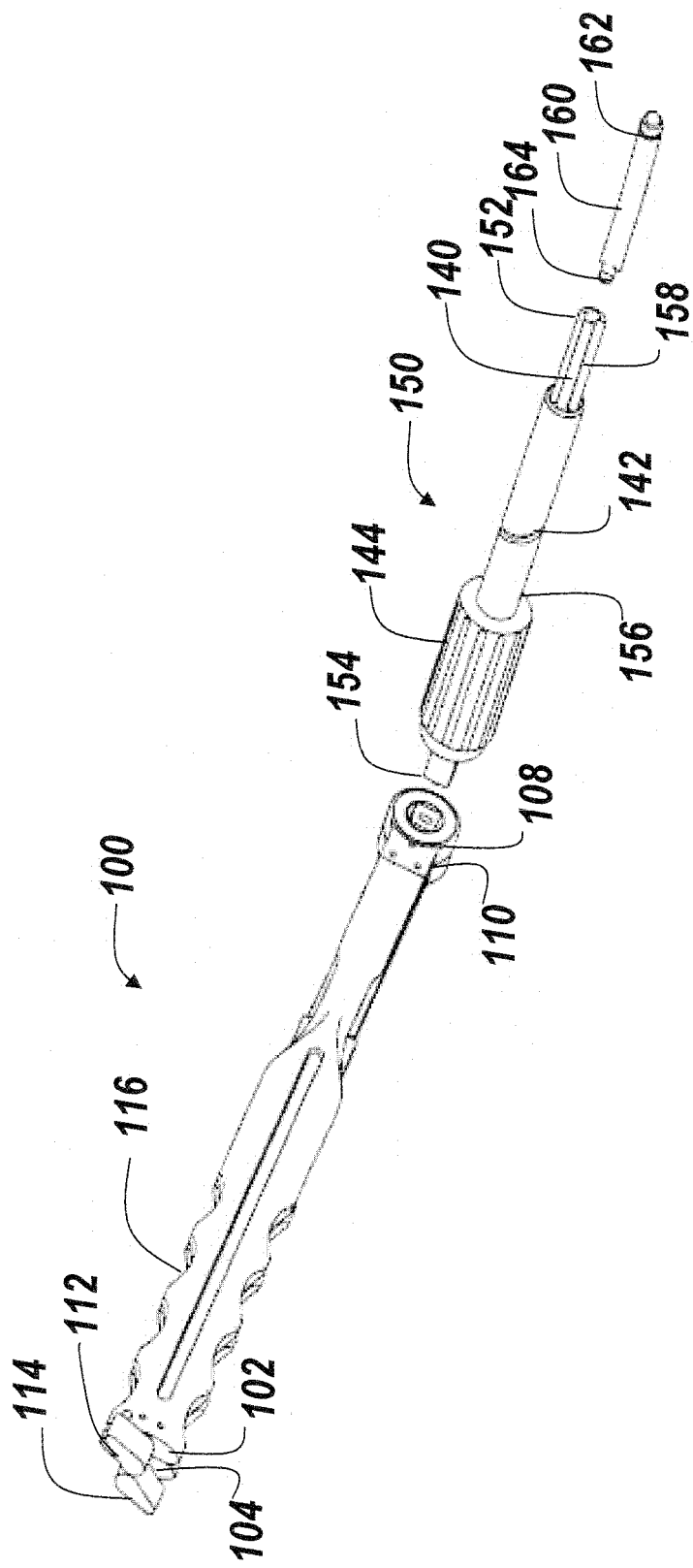
FIGS. 1A-1B illustrate an exemplary spinal fixation element rotation instrument, an exemplary extension element and an exemplary spinal fixation element.

Exemplary embodiments of the present invention provide an improved spinal fixation element rotation instrument to be used in placing a spinal fixation element through a plurality of vertebral bone anchors during a minimally invasive surgery for correcting a deformity or a degenerative spine disorder. One of ordinary skill in the art will recognize that the present invention is not limited to use in spinal surgery, and that the instrument and methods described herein can be adapted for use with any suitable surgical device to be placed in a desired position in a variety of medical procedures.

The spinal fixation element rotation instrument of some of the exemplary embodiments has two lever arms that are connected to each other at distal ends thereof. Each lever arm rotates relative to the other lever arm. The distal ends of the first and second lever arms are adapted to couple to a spinal fixation element or an extension element that couples to the spinal fixation element. The spinal fixation element is secured within the distal ends of the first and second lever arms. The distal ends of the lever arms may have a dual ratchet feature that prevents rotation of the spinal fixation element in a set direction. When one arm, i.e. the driver, rotates back and forth, the other arm, i.e. the holder, is held stationary. As a result, the spinal fixation element rotates in a predetermined direction from an initial position to a rotated position and is prevented from rotating back toward the initial position.

The rotational direction of the lever arms, thus the rotational direction of the spinal fixation element, may be set using knobs or switches provided at a proximal end of one or both of the lever arms. Setting the switch of the driver arm to a first position may allow the driver arm to rotate the spinal fixation element clockwise. Similarly, setting the switch of the driver arm to a second position may allow the driver arm to rotate the spinal fixation element counterclockwise.

According to various embodiments of the present invention, the switches provided on the first and second lever arms may be set in a position that locks the rotation of the lever arms. In the locked out position, the lever arms no longer have the ratcheting feature and the spinal extension element is prevented from rotating within the distal ends of the lever arms. Therefore, if the user would like to change the rotational direction of the spinal fixation element, the user would have to change the rotational direction of one of the driver arm or the holder arm. If the user only changes the rotational direction of both of the driver arm and the holder arm, the instrument will be in the locked out position.

The driver arm of the spinal fixation element rotation instrument may be provided with two sections attached to each other via a hinge or a loaded spring mechanism. The hinge may allow the first section to rotate about a central axis of the hinge, relative to the second section. This way, the first section may be moved away from the screw extensions providing clearance during spinal fixation element rotation and enabling the user to relocate the first section to better suit the conditions of the procedure.

FIG. 1A illustrates a profile view of an exemplary spinal fixation element rotation instrument 100, an exemplary extension element 150 and an exemplary spinal fixation element 160. A proximal end 154 of the extension element 150 couples to the spinal fixation element rotation instrument 100 and a distal end 152 of the extension element 150 couples to the spinal fixation element 160.

Figure 1B:
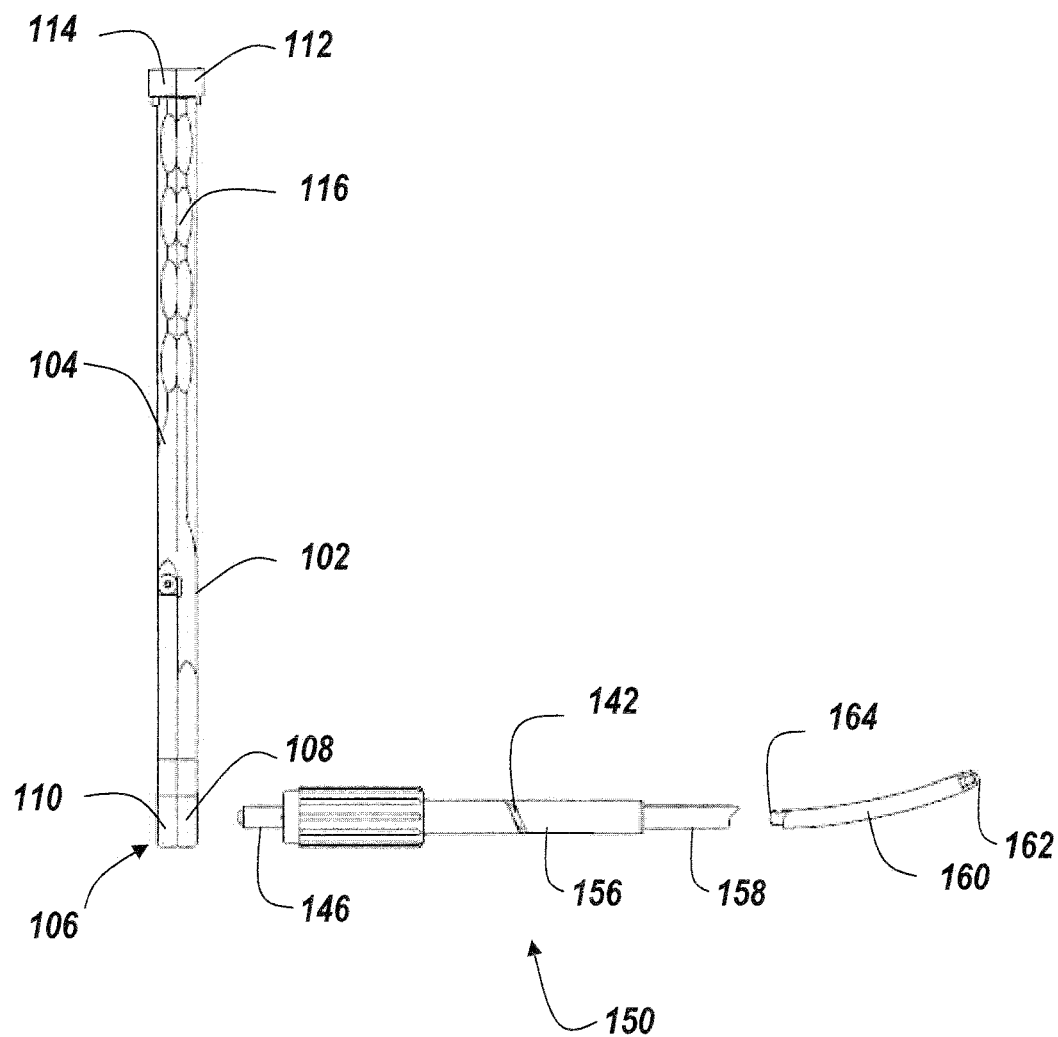

As illustrated in FIGS. 1A-1B, the extension element 150 includes a sleeve 156 provided around a carrier 158. The carrier 158 is adapted to couple to the spinal fixation element 160. The carrier 158 may include a coupling feature 140, such as a leaf spring, for tightly holding the spinal fixation element 160. The coupling feature 140 prevents inadvertent decoupling of the spinal fixation element 160 from the extension element 150. For example, the spinal fixation element 160 may be coupled to the extension element 150 via a spring loaded tooth. Alternatively, the coupling feature 140 may grab on the surface features provided at the proximal end 164 of the spinal fixation element 160. Exemplary coupling mechanisms coupling the extension element 150 and the spinal fixation element 160 according to various embodiments of the present invention will be described below.

The sleeve 156 may be slid over the carrier 158 upon the carrier 158 couples to the spinal fixation element 160. As such, the location where the carrier 158 engages the spinal fixation element 160 is protected by the sleeve 156 to prevent inadvertent decoupling of the spinal fixation element 160 from the carrier 158. In an exemplary embodiment of the present invention, the sleeve 156 may include an angular cut 142 and the carrier 158 may include a protrusion, such as a pin, that slides in the angular cut 142 of the sleeve 158. The pin and the angular cut 142 allow the sleeve 156 to move forward and backward over the carrier 158. The pin moves within the angular cut 142 when the user twists and slides the sleeve 156 over the carrier 158. The sleeve 156 may be provided with a grooved surface portion 144 to improve the user's grip on the extension element 150 and to facilitate twisting of the sleeve 156 over the carrier 158.

The spinal fixation element rotation instrument 100 illustrated in FIGS. 1A-1B is formed of two lever arms 102 and 104. The first lever arm 102 and the second lever arm 104 may be provided with surface features 116 for improved ergonomics and improved control over the spinal fixation element rotation instrument 110. A first ratchet 108 is provided at the distal end of the first lever arm 102. A second ratchet 110 is provided at the distal end of the second lever arm 104. The first ratchet 108 and the second ratchet 110 are coupled to each other. The proximal end 154 of the extension element 150 couples to the spinal fixation element rotation instrument 100 by fitting through the first ratchet 108 and the second ratchet 110. The rotation of the first ratchet 108 and/or the second ratchet 110 rotates the spinal fixation element 160 coupled to the extension element 150. The rotational direction of the spinal fixation element 160 depends on the rotational direction of the first ratchet 108 and/or the second ratchet 110. One of ordinary skill in the art will appreciate that the first ratchet 108 and the second ratchet 110 may couple to a variety of modular tips and that the modularity is not limited to the extension element 150.

The extension element 150 may be provided with a plurality of markers to illustrate how much the extension element 150 has rotated within the distal end 106 of the spinal fixation element rotation instrument 100.

The extension element 150 may also include a coupling/decoupling mechanism 146 for coupling and decoupling the extension element 150 to/from the spinal fixation element rotation instrument 100. FIG. 2A illustrates a cross-sectional view of the extension element 150 coupled to the distal end of the spinal fixation element rotation instrument 100. FIG. 2B illustrates a cross-sectional view of the extension element 150 and the decoupling mechanism 146 provided at a proximal end 154 of the extension element 150. FIG. 2C illustrates a cross-sectional view of the distal end 106 of the spinal fixation element rotation instrument 100. The coupling/decoupling mechanism 146 may comprise a loaded spring 200 that is used to lock the extension element 150 in the distal end 106 of the spinal fixation element rotation instrument 100. By pressing on the coupling/decoupling mechanism 146, the user compresses the loaded spring 200. When the user places the extension element 150 through the distal end 106 of the spinal fixation element rotation instrument 100, the loaded spring 200 decompresses and pushes the ball 147 provided on a proximal end 154 of the extension element 150 outward. As illustrated in FIG. 2C, one or more grooves 107 may be provided in an internal surface of the first ratchet 108 and/or the second ratchet 110. The ball 147 falls into one of the grooves 107 provided on the internal surface of the distal end 106 of the spinal fixation element rotation instrument 100. When the ball 147 is in the groove 107, the extension element 150 is locked in the distal end 106 of the spinal fixation element rotation instrument 100. The user may press on the coupling/decoupling mechanism 146 to disengage the ball 147 from the groove 107, unlocking the extension element 150 from the spinal fixation element rotation instrument 100.

One of ordinary skill in the art will appreciate that the coupling/decoupling mechanism 146 described above is for illustrative purposes only and similar mechanisms may be used to couple the extension element 150 to the spinal fixation element rotation instrument 100. Moreover, the proximal end 154 of the extension element 150 may have a variety of shapes and sizes. The spinal fixation element rotation instrument 100 may be provided with an appropriate distal end 106 that matches the shape and size of the proximal end 154 of the extension element 150.

According to various embodiments of the present invention, additional modular tips may be provided to facilitate the coupling between the spinal fixation element rotation element 100 and the extension element 150. A first end of the modular tip couples to the distal end of the spinal fixation element rotation instrument 100 and a second end, opposite to the first end, couples to the proximal end of the extension element 150. The first and second ends of the modular tips may be, for example, circular, hexagonal, diamond shape, etc. according to the shape of the distal end 106 of the spinal fixation element rotation instrument 100 and the proximal end 154 of the extension element 150.

According to another exemplary embodiment of the present invention, the spinal fixation element rotation instrument 100 may directly couple to the spinal fixation element 160 eliminating the extension element 150. In this exemplary embodiment, the spinal fixation element 160 may fit through a portion of the first ratchet 108 and/or the second ratchet 110. The spinal fixation element 160 may have surface features such as threads or grooves that enable a portion of the first ratchet 108 and/or the second ratchet 110 to grab on the spinal fixation element 160. The spinal fixation element 160 may be of any shape and size, including but not limited to, hexagonal, square, round, diamond, etc.

Figure 4A:
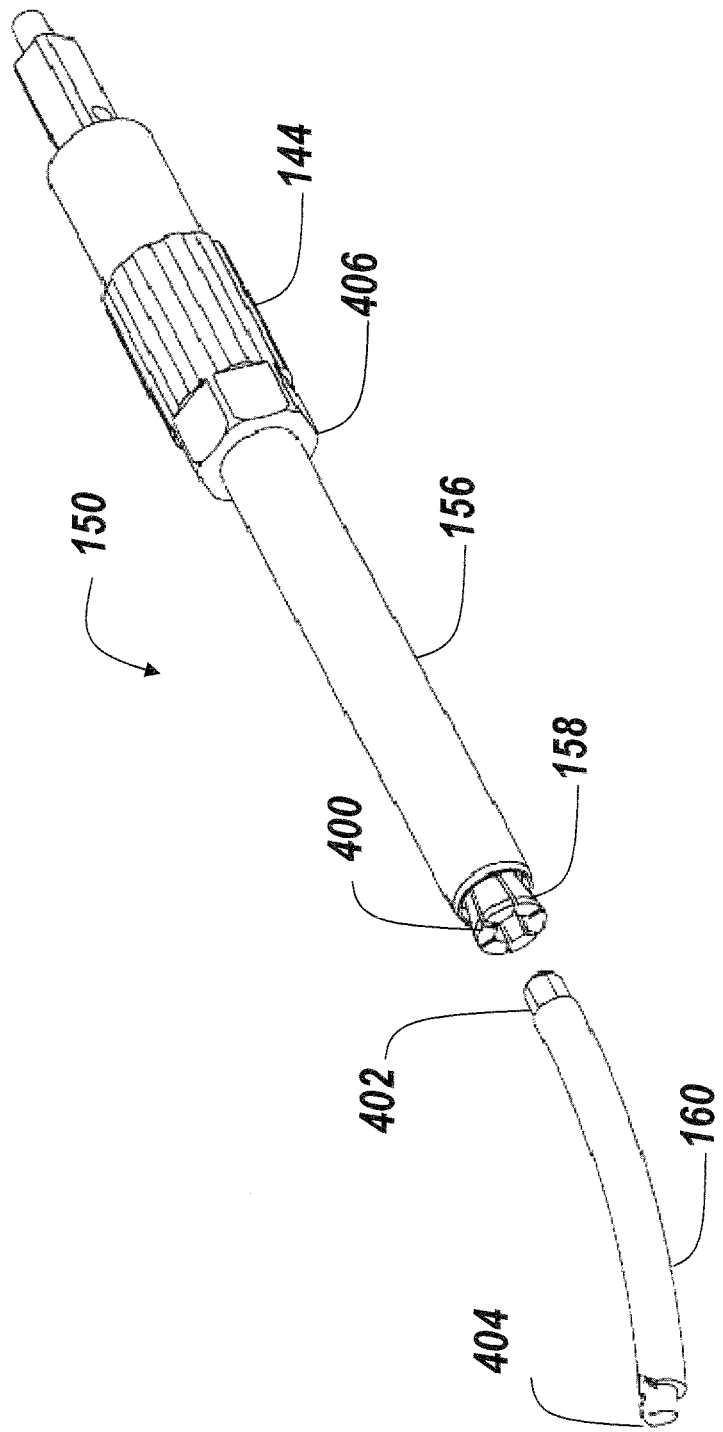
Figure 4B:
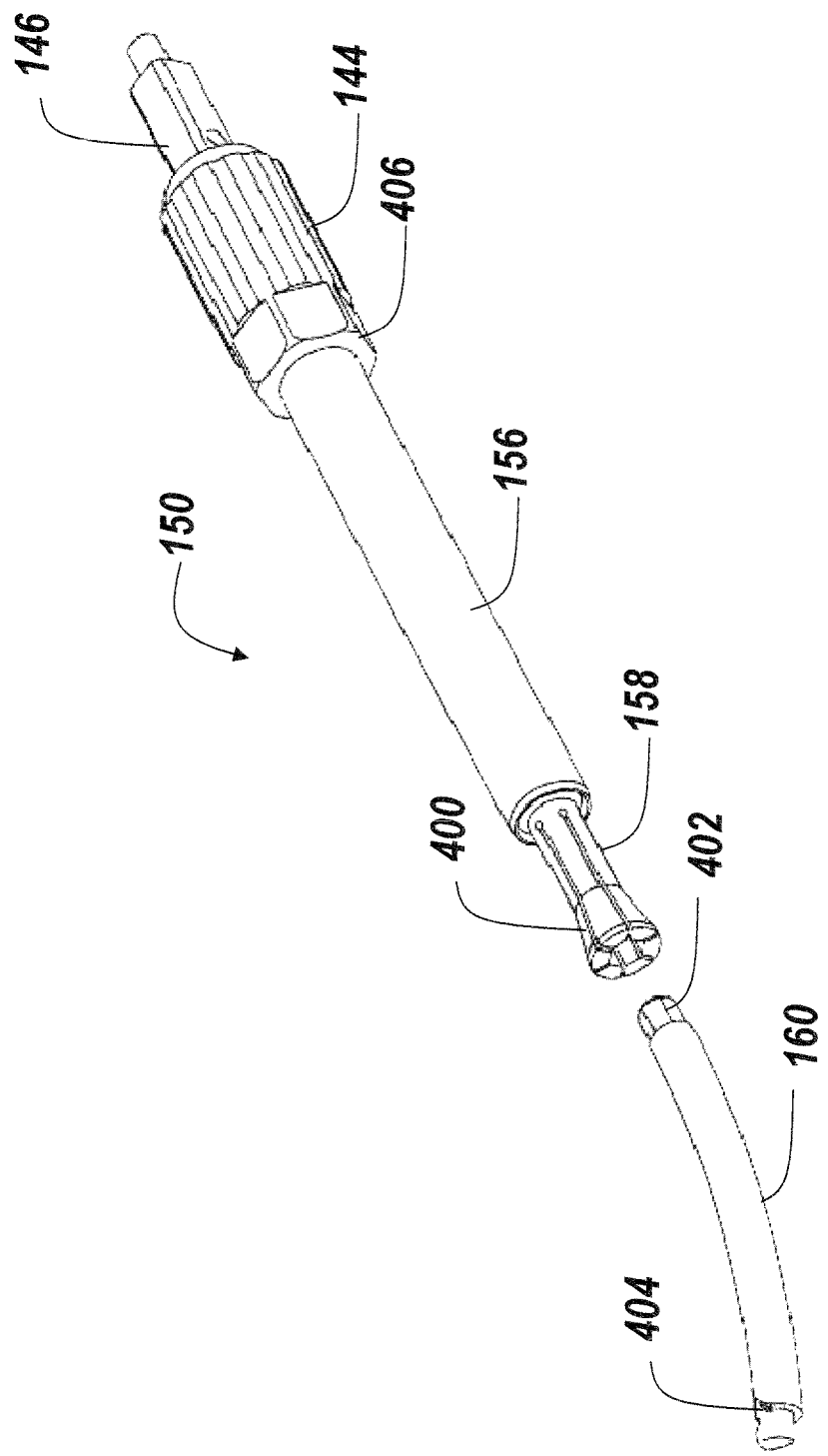

FIGS. 3A-3B illustrate two exemplary spinal fixation elements 160 according to various embodiments of the present inventions. As illustrated in FIG. 3A, the proximal end 164 of the spinal fixation element 160 may have a hexagonal shape. FIG. 3B illustrates an embodiment of the present invention where the spinal fixation element 160 is provided with a rounded proximal end 166. The distal end 162 of the spinal fixation elements 160 illustrated in FIGS. 3A and 3B may be of any shape. According to various embodiments of the present application, the spinal fixation elements, such as those illustrated in FIGS. 3A and 3B, may also be used by reversing the distal end and the proximal end of the spinal fixation elements. FIGS. 4A-4C illustrate an exemplary embodiment where the distal end 164 of the spinal fixation element 160 illustrated in FIG. 3A becomes the proximal end 402 and is coupled to the extension element 150. The proximal end 162 of the spinal fixation element 160 illustrated in FIG. 3A becomes the distal end 404 and is inserted into the patient.

FIGS. 4A-4C illustrate an exemplary mechanism 400 to couple the spinal fixation element 160 to the extension element 150. As illustrated in FIG. 4A, the carrier 158 is provided with a grabbing tip 400. The grabbing tip 400 assumes a larger diameter when the sleeve 156 is retracted over the carrier 158, as illustrated in FIG. 4B. The proximal end 402 of the spinal fixation element 160 is inserted in the grabbing tip 400 when the grabbing tip 400 is at an extended position. The sleeve 156 is then advanced over the carrier 158 and the grabbing tip 400 so as to cover the grabbing tip 400. When the sleeve 156 is pushed over the grabbing tip 400, the opening of the grabbing tip 400 closes over the proximal end 402 of the spinal fixation element 160 so as to tightly grab the spinal fixation element 160.

A portion of the exemplary sleeve 156 illustrated in FIGS. 4A-4C may be provided with a plurality of threads. The treads may be 5-10 mm. long, provided on a portion of the inner surface of the sleeve 156. The threads may engage a portion of the carrier 158. The threads may slowly disengage from the carrier 158 while the sleeve 156 is retracted over the carrier 158 to expose the grabbing tip 400. When the threads are completely disengaged from the carrier 158, the sleeve 156 may be pulled up to expose the remainder of the carrier 158. The threads may help the sleeve 156 to tighten or loosen up around the carrier 158 and the grabbing tip 400.

The grooved surface portion 144 of the sleeve 156 may provide improved control to the user over the sleeve 156. The user may twist and rotate the sleeve 156 around the carrier 158 using the grooved surface portion 144 so as to advance or retract the sleeve 156 over the carrier 158. The extension element 150 illustrated in FIGS. 4A-4C may have a coupling/decoupling mechanism 146 similar to one discussed above to couple the extension element 150 to the spinal fixation element rotation instrument 100. The sleeve 156 may also include an external surface feature 406 for mating with a second instrument when the spinal fixation element 160 is in its final place and the extension element 150 needs to be removed. During removal of the extension element 150, it may be difficult for the surgeon to get their hand to a position where the surgeon can loosen the sleeve 156 and detach the spinal fixation element 160 from the extension element 150. If this is the case, the second instrument, e.g. a hex wrench that mates with the external surface feature 406 of the sleeve 156, may be used to grab on the sleeve 156 for rotating it to release the extension element 150 from the sleeve 156.

FIGS. 5A-5B illustrate another exemplary mechanism 500 to couple the spinal fixation element 160 to the extension element 150. As illustrated in FIG. 5B, the internal surface of the carrier 158 is provided with a leaf spring 502. The proximal end 164 of the spinal fixation element 160 is provided with a notch 504. When the spinal fixation element 160 is coupled to the extension element 150, the leaf spring 502 of the carrier 158 grabs the notch 504 provided on the proximal end 164 of the spinal fixation element 160. The coupling location of the spinal fixation element 160 and the extension element 150 is provided within the sleeve 156 to prevent unintentional decoupling of the spinal fixation element 160 from the extension element 150.

FIGS. 6A-6B illustrate a top view of the spinal fixation element rotation instrument 100. The first lever arm 102 includes a switch or a knob 112 at the proximal end thereof. Similarly, the second lever arm 104 includes a switch or a knob 114 at the proximal end thereof. The switch 112 is used to adjust the rotational direction of the first ratchet 108. Similarly, the switch 114 is used to adjust the rotational direction of the second ratchet 110. Using the switch 112, the first ratchet 108 may be set to rotate clockwise or counterclockwise. Using the switch 114, the second ratchet 110 may be set to rotate clockwise or counterclockwise. The rotation of the first ratchet 108 or the rotation of the second ratchet 110 rotates the spinal fixation element 160 that is coupled to the spinal fixation element rotation instrument 100.

Figure 6C:
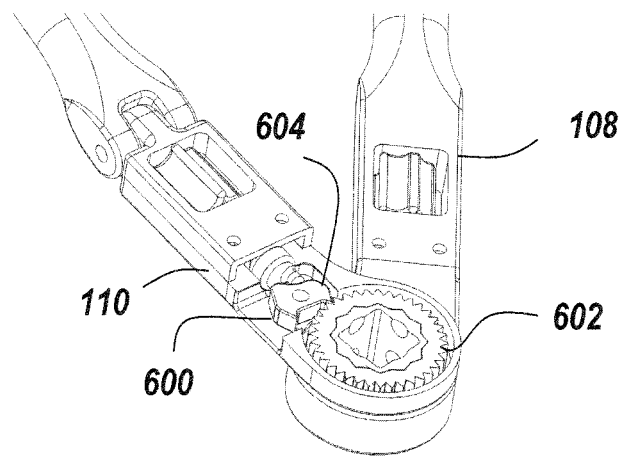
FIGS. 6C-6D illustrate a first ratchet and a second ratchet provided at a distal end of the spinal fixation element rotation instrument according to an exemplary embodiment of the present invention.
Figure 6D:
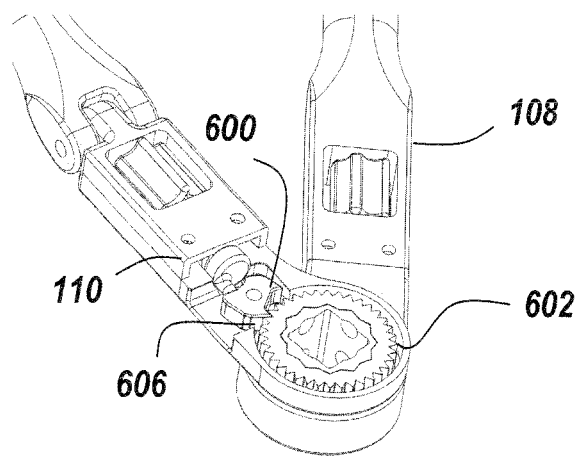

As shown in FIG. 6C, when the second ratchet 110 is set to rotate in a first direction, i.e. clockwise, a right end 604 of the rocker 600 engages the teeth 602 of the second ratchet 110. Clockwise rotation of the second ratchet 110 rotates the spinal fixation element 160 clockwise. As shown in FIG. 6D, when the second ratchet 110 is set to rotate counterclockwise, a left end 606 of the rocker 600 engages the teeth 602 of the second ratchet 110. Counterclockwise rotation of the second ratchet 110 rotates the spinal fixation element 160 counterclockwise. As such, it is possible to control the rotational direction of the spinal fixation element 160 using the switches 112 and 114 of the spinal fixation element rotation instrument 100.

The rotational direction of the ratchets 108 and 110 is controlled with the first switch 112 and 114, respectively. When the first ratchet 108 is set to rotate in a first direction and the second ratchet 110 is set to rotate in a second direction opposite to the first direction, the first ratchet 108 and the second ratchet 110 may lock each other out. When the ratchets 108 and 110 are at a locked out position, the spinal fixation element 160 may no longer be rotated in the distal end 106 of the spinal fixation element rotation instrument 100.

Figure 7:
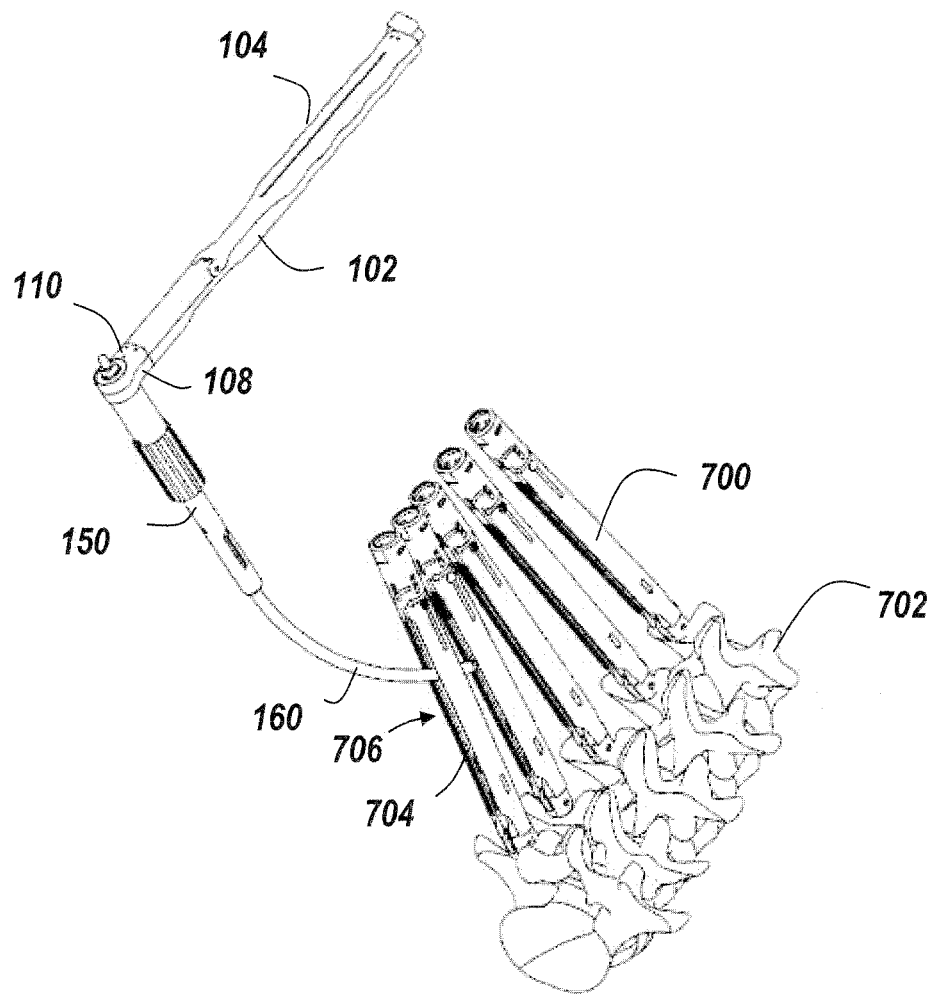
FIG. 7 illustrates an exemplary spinal fixation element rotation element coupled to the exemplary extension element that is coupled to the exemplary spinal fixation element.

FIG. 7 illustrates an exemplary embodiment of the spinal fixation element rotation instrument 100. As illustrated in FIG. 7, the distal end of the spinal fixation element rotation instrument 100 couples to the proximal end 154 of the extension element 150. The proximal end 154 of the extension element 150 passes through and protrudes from the first ratchet 108 and the second ratchet 110 provided at the distal end of the spinal fixation element rotation instrument 100. The carrier 158 of the extension element 150 is coupled to the spinal fixation element 160 that will be implanted during a minimally invasive surgery to correct a spinal deformation or degeneration. A plurality of bone anchors 700 are implanted on the vertebrae 702. Each bone anchor 700 includes an opening 704 provided above the bone surface. The openings 704 of the adjacent bone anchors 700 form a passage 706. The spinal fixation element 160 is fed through the passage 706 using the spinal fixation element rotation element 100. If the user wants to merely advance spinal fixation element 160 in the passage 706, the user may set the lever arms 102 and 104 to rotate in opposite direction so as to put the spinal fixation element rotation instrument 100 in a locked out position. In the locked out position, the spinal fixation element rotation element 100 serves as a spinal fixation element holder. The spinal fixation element may be introduced through the incision using the spinal fixation element rotation element 100 at the locked out position. In addition, the spinal fixation element rotation element 100 at the locked out position may facilitate the translation of the rod from a first bone anchor to the adjacent next bone anchor. The user may still rotate the spinal fixation element 160 by rotating the spinal fixation element rotation element 100 similar to a spinal fixation element holder. This will allow the user to move the spinal fixation element 160 in the surgical site as necessary. However, when it is necessary to controllably rotate the spinal fixation element 160 in the passage 706, the first and second lever arms 102 and 104 of the spinal fixation element rotation element 100 may be set to rotate in the same direction so as to rotate the spinal fixation element 160.

If the user wants to rotate the spinal fixation element 160 clockwise, the driver arm, e.g. the second lever arm 104, is rotated clockwise while the holder, e.g. the first lever arm 102, is held stationary. The clockwise rotation of the driver arm rotates the second ratchet 110 clockwise. The extension element 150 and the spinal fixation element 160 are provided in the socket of the second ratchet 110. The clockwise rotation of the second ratchet 110 rotates the spinal fixation element 110 clockwise. The first ratchet 108 attached to the holder arm keeps the extension element 150 and the spinal fixation element 160 from rotating back toward their initial position, i.e. rotating counterclockwise. The driver arm, e.g. the second lever arm 104, is rotated counterclockwise toward to start position to rewind the second ratchet 110. These steps are repeated for further rotating the rod clockwise.

If the user wants to rotate the spinal fixation element 160 counterclockwise, the driver arm, e.g. the second lever arm 104, is rotated counterclockwise while the holder, e.g. the first lever arm 102, is held stationary. The counterclockwise rotation of the driver arm rotates the second ratchet 110 counterclockwise. The extension element 150 and the spinal fixation element 160 are provided in the socket of the second ratchet 110. The counterclockwise rotation of the second ratchet 110 rotates the spinal fixation element 110 counterclockwise. The first ratchet 108 attached to the holder arm keeps the extension element 150 and the spinal fixation element 160 from rotating back toward their initial position, i.e. rotating clockwise. The driver arm, e.g. the second lever arm 104, is rotated clockwise toward to start position to rewind the second ratchet 110. These steps are repeated for further rotating the rod counterclockwise.

Using a ratchet with the holder arm results in improved control over the extension element 150 and the spinal fixation element 160. However, according to various embodiments of the present invention, the holder arm may be provided with other mechanisms, such as a strap wrench, instead of a ratchet to interface with the extension element 150. The holder arm is configured to keep the spinal fixation element 160 or the extension element 150 coupled to the spinal fixation element rotation instrument 100 in place. One of ordinary skill in the art will appreciate that other mechanisms, such as a strap wrench or a rotation mechanism may be provided at a distal end of the driver arm.

Figure 8A:
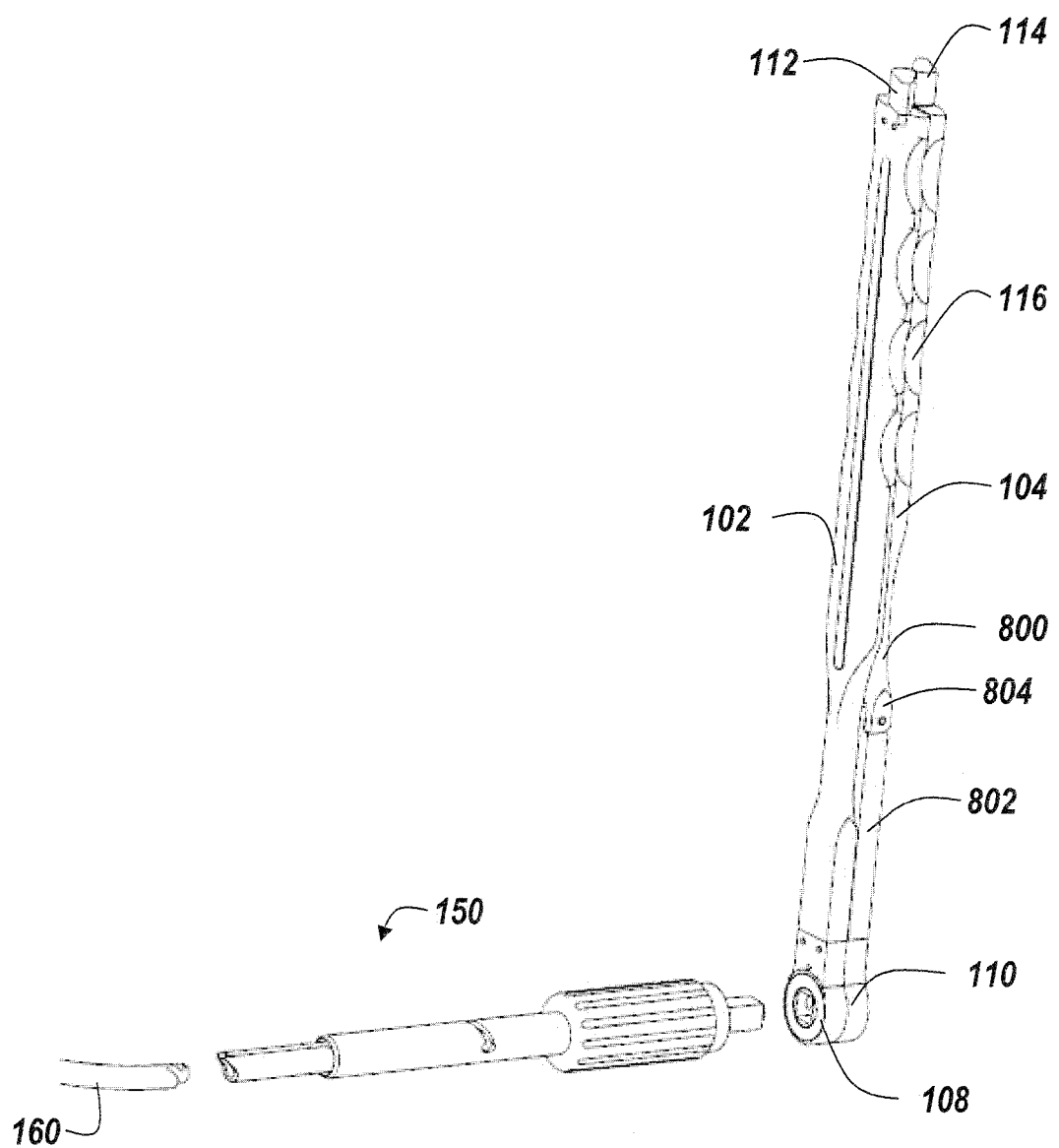
FIGS. 8A-8B illustrate an exemplary configuration of a second lever arm including a first section and a second section.
Figure 8B:
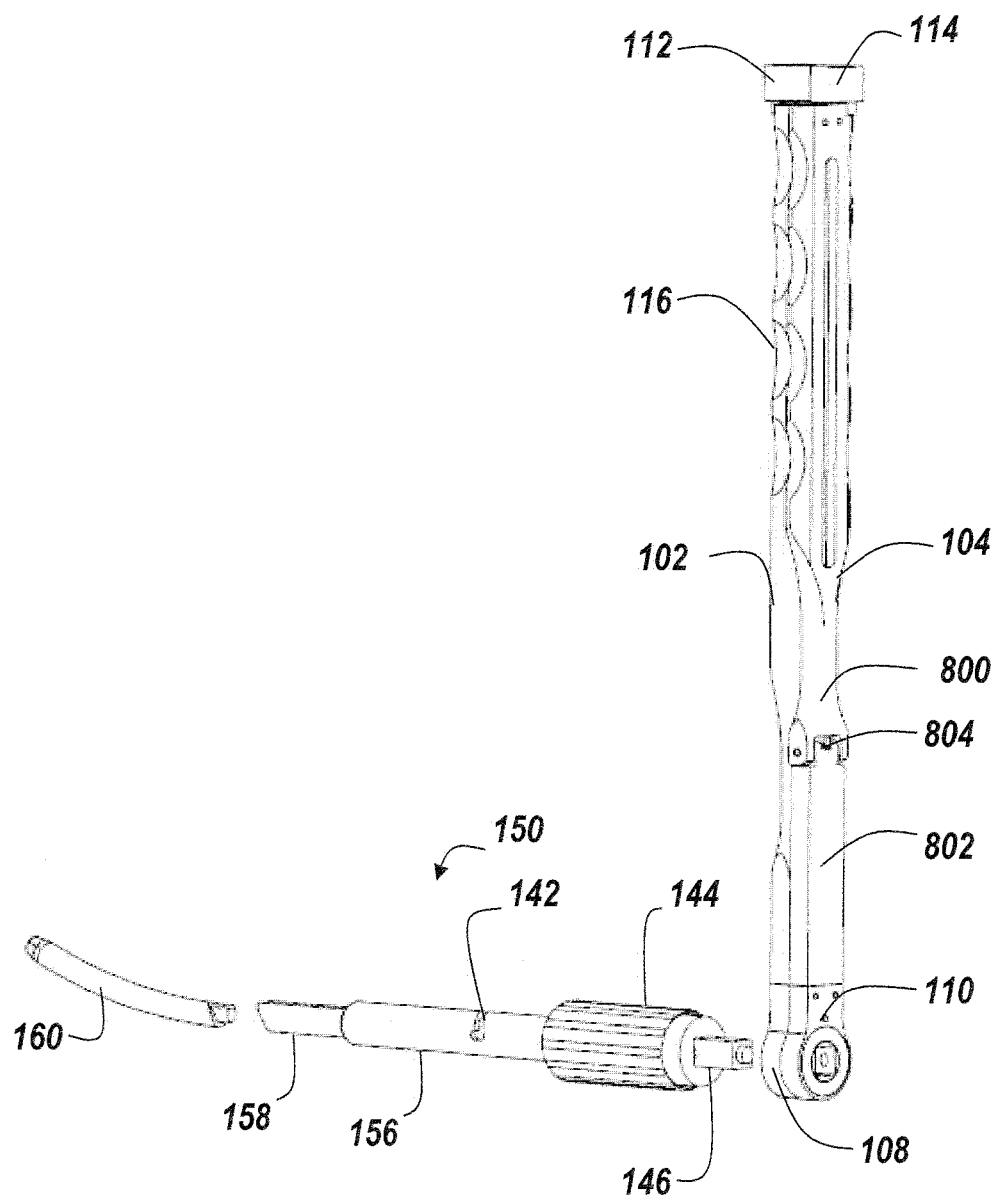

FIGS. 8A-8C illustrate another exemplary embodiment of the spinal fixation element extension instrument 100. As illustrated in FIGS. 8A-8C, the driver arm, e.g. the second lever arm 104, may include a first section 800 and a second section 802 that are coupled together using an attachment mechanism 804 such as a hinge or a loaded spring mechanism. The first section 800 may be rotated about a central axis of the attachment mechanism 804 so as to be positioned at an angle relative to the longitudinal axis of the second section 802. At the angled position, the first section 800 may serve as a handle for rotating the second ratchet 110 about the central axis thereof.

Alternatively, the driver arm, e.g. the second lever arm 104 may be a monolithic element. A handle may be attached to the second lever arm 104 for easily rotating the second lever arm 104. The handle may be fixed to the second lever arm 104. Alternatively, the handle may be attached to the second lever arm 104 using an attachment mechanism such as a hinge so as to be positioned at various angles relative to the second lever arm 104. The handle may enable the user to better maneuver the spinal fixation element rotation instrument 100.

Figure 9A:
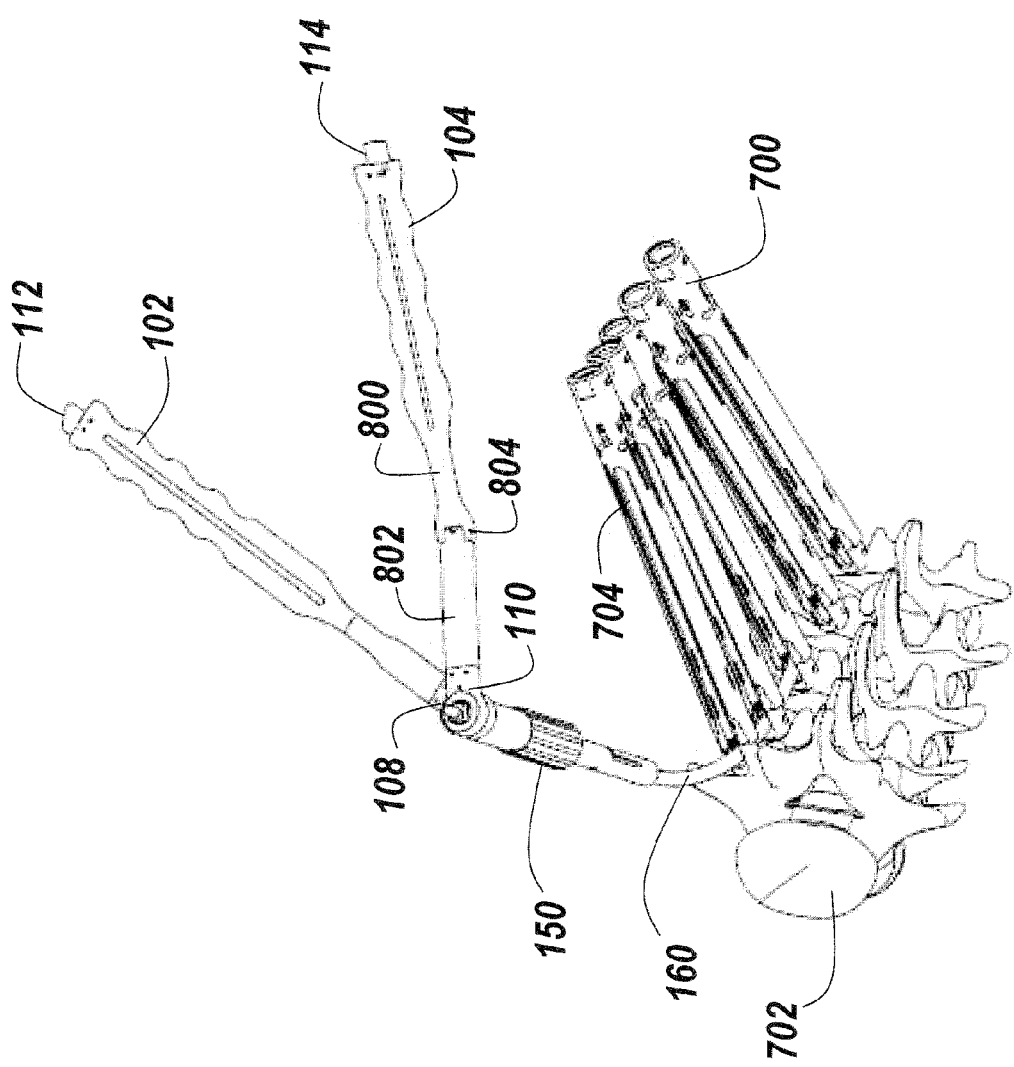
FIGS. 9A-9B illustrate the second section of the second lever arm at an angled position relative to the first section of the second lever arm.
Figure 9B:
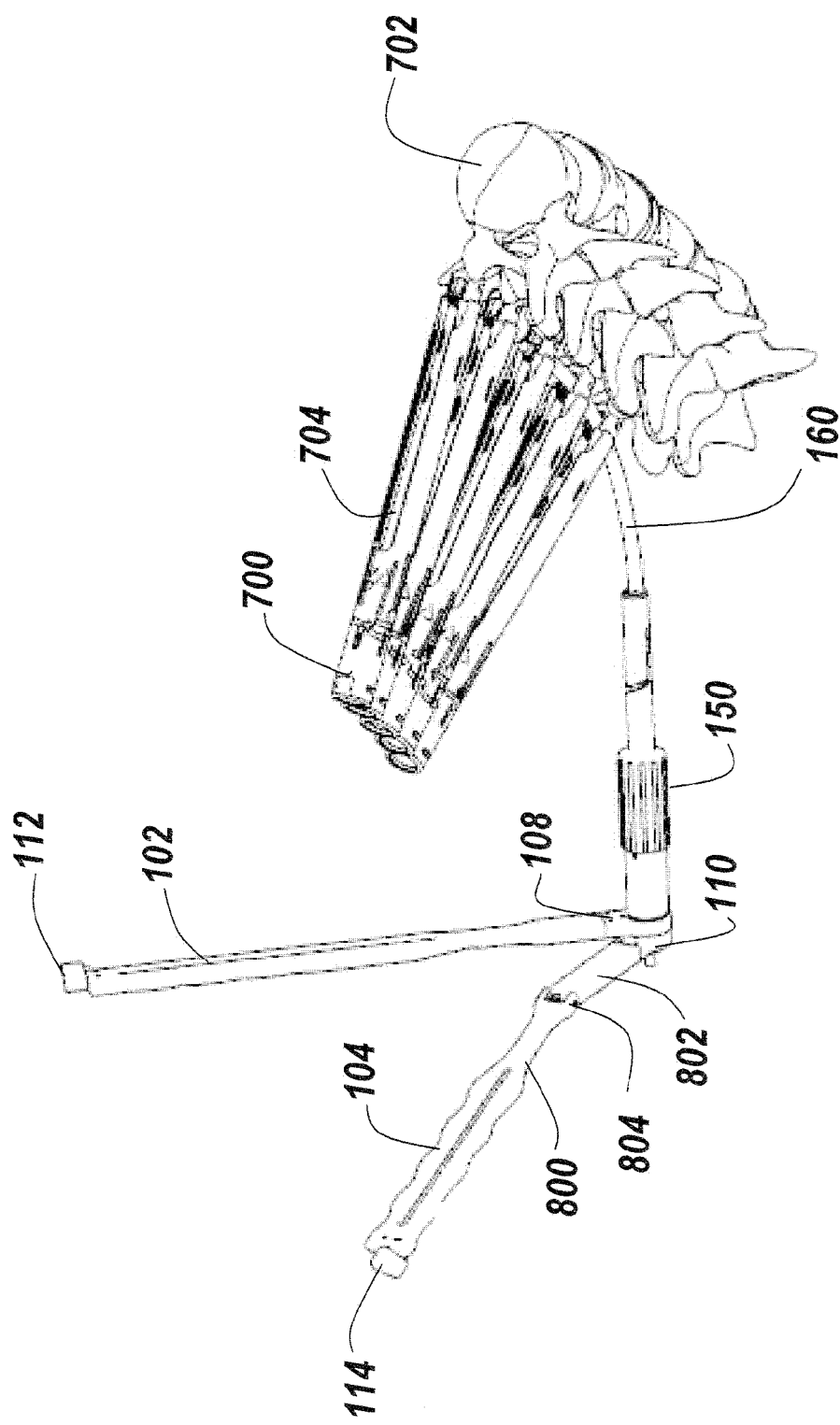

FIGS. 9A-9B illustrate an exemplary embodiment of the spinal fixation element extension instrument 100 where the first section 800 of the second lever arm 104 is provided at an angle about 15° relative to the second section 802. The first section 800 may be rotated about the central axis of the attachment mechanism 804 so as to form an angle about 0°-45°, and preferably about 0°-15°, with the longitudinal axis of the second section 802. However, the positioning of the first section 800 is not limited to the angle illustrated in the figures. The first section 800 may be positioned at various angles relative to the longitudinal axis of the second section 802 to better suit the conditions of the procedure.

In the exemplary embodiment illustrated in FIGS. 9A-9B, the first lever arm 102, i.e. the holder, is held stationary while the second lever arm 104, i.e. the driver, is rotated about the central axis of the first ratchet 108 and the second ratchet 110 using the first section 800 of the second lever arm 104. The attachment mechanism 804 holds the first section 800 in place relative to the second section 802. With the rotation of the second ratchet 110, the extension element 150 and the spinal fixation element 160 are rotated.

FIGS. 9A-9B illustrate the spinal fixation element 160 placed through the first three bone anchors 700. While the second ratchet 110 enables the spinal fixation element 160 to rotate in a first direction, the first ratchet 108 keeps the extension element 150 from rotating back toward its initial position in a second direction opposite to the first direction. Thus, the first ratchet 108 prevents the spinal fixation element 160 from inadvertently rotating in the second direction when the spinal fixation element 160 is in the passage 706. However, if the spinal fixation element 160 is not placed as desired, the surgeon may retract the spinal fixation element 160 in the passage 706 using the spinal fixation element rotation instrument 100 as a spinal fixation element holding tool. The surgeon may rotate the spinal fixation element 160 as many times as necessary using the spinal fixation element rotation instrument 100 to place the spinal fixation element 160 in the desired position.

Figure 10A:
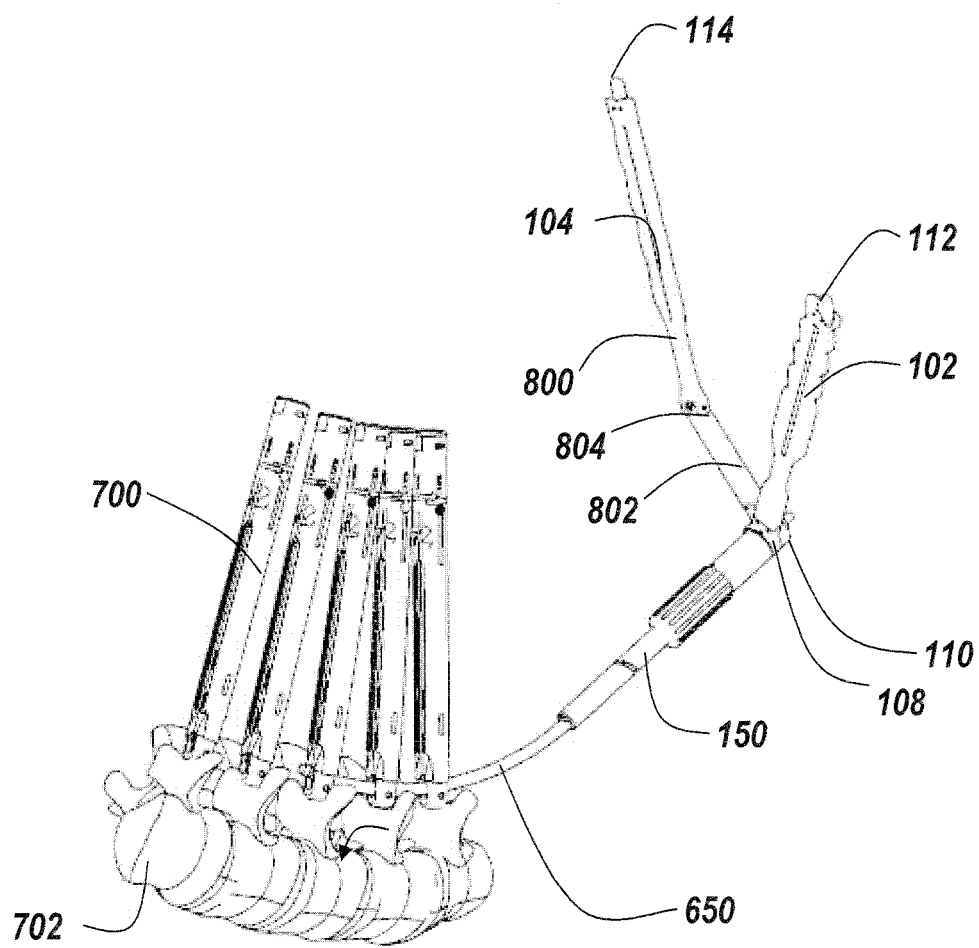
FIGS. 10A-10B illustrate the placement of the spinal fixation element through a plurality of bone anchors using the spinal fixation element rotation instrument.
Figure 10B:
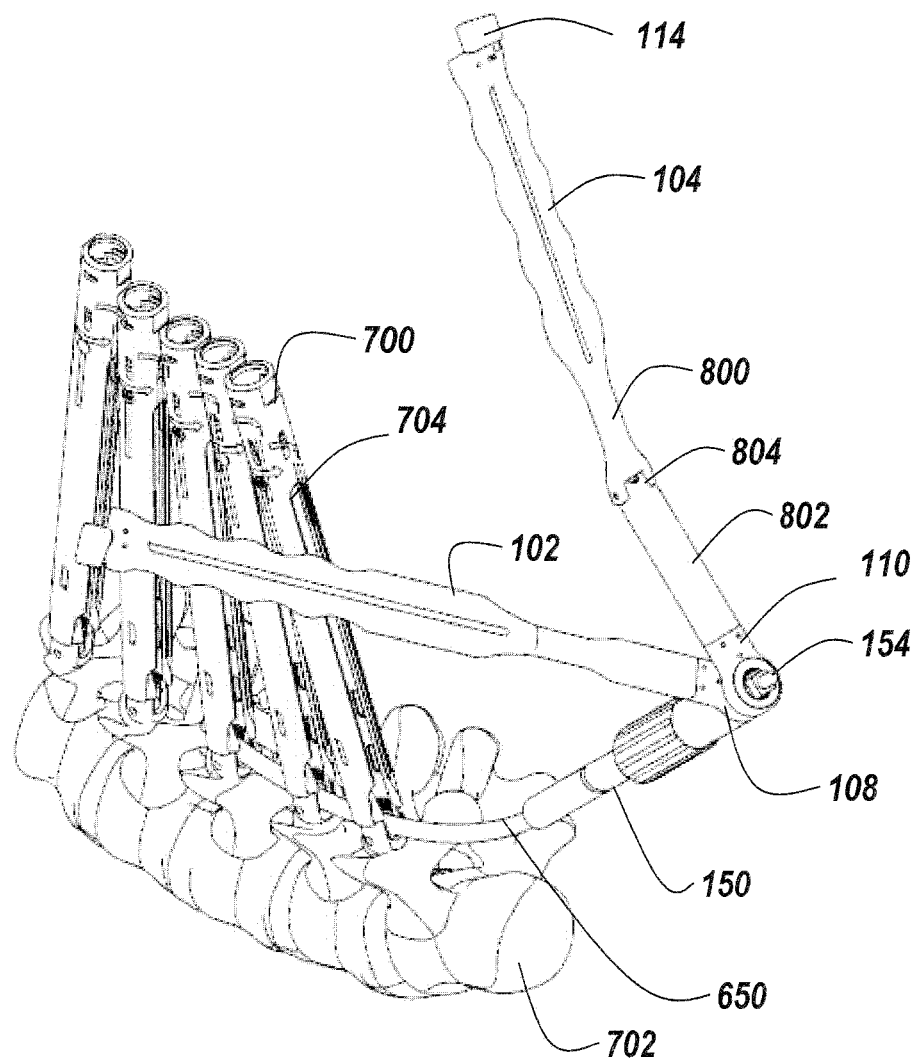

The spinal fixation element rotation instrument 100 of the present invention may be used with a variety of spinal fixation elements. A type of spinal fixation element is a curved spinal fixation element 650 illustrated in FIGS. 10A-10B. Due to the curvature of the curved spinal fixation element 650 or the curvature of the spine at the target location, it may be preferable to insert the curved spinal fixation element 650 through the skin incision in a first position, such as a concave position. Once the curved spinal fixation element 650 is placed through the openings 704 of one or more bone anchors 700, the curved spinal fixation element 650 may be rotated to an inverted position, such as a convex position, using the spinal fixation element rotation instrument 100. The curved spinal fixation element 650 may be rotated under the skin as many times as necessary to accommodate the spinal curvatures.

Figure 11B:
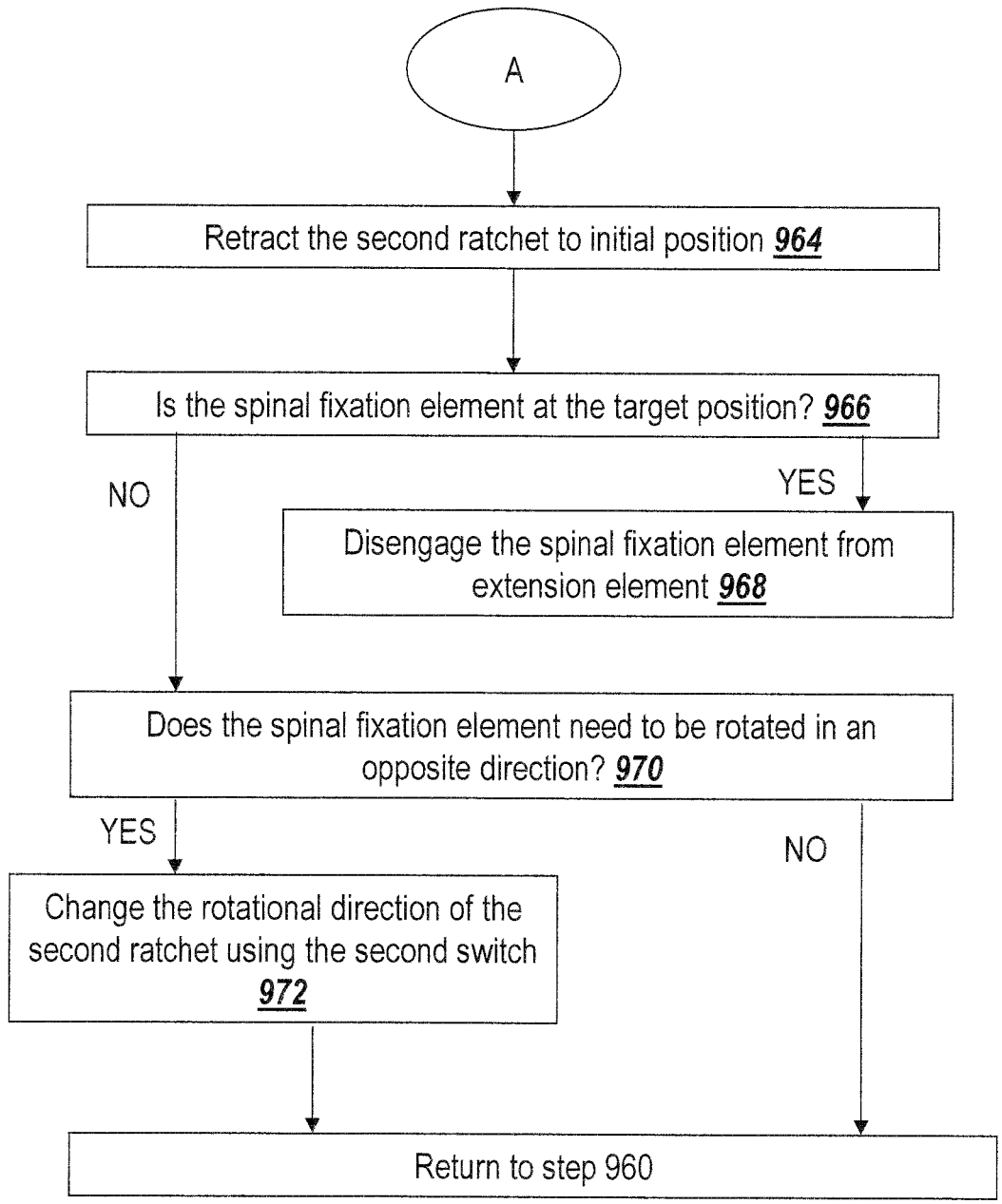

FIGS. 11A-11B illustrate a flowchart 950 of steps for placing a spinal fixation element through a plurality of bone anchors. Each bone anchor has an opening for receiving the spinal fixation element. The user first sets the rotational direction of the first ratchet and the second ratchet of the spinal fixation element rotation instrument. The first ratchet and the second ratchet of the spinal fixation element rotation instrument may be set to rotate clockwise (step 952). The rotational direction of the ratchets is for illustrative purposes only. The ratchets may be configured to achieve the same results when the ratchets are set to rotate counterclockwise. According to the embodiments of the present invention, when the ratchets are set to rotate in opposite directions, the ratchets lock each other out. One of ordinary skill in the art will appreciate that the rotational directional of the ratchets are for illustrative purposes only and that the ratchets may be configured to lock each other out when they are set to rotate in the same direction.

The spinal fixation element rotation instrument is then coupled to the extension element (step 954). The extension element may already be coupled to the spinal fixation element. Alternatively, the extension element may be coupled to the spinal fixation element after the spinal fixation element rotation instrument is coupled to the extension element (step 956). The spinal fixation element and a portion of the extension element are inserted through a skin incision (step 958).

During the minimally invasive surgeries, it is possible to insert the spinal fixation element and a portion the extension element through a small skin incision without inserting the spinal fixation element rotation instrument through the skin incision, thus reducing the trauma to the tissue at the surgery site. Once under the skin, the spinal fixation element is placed through a bone anchor opening (step 960). If it is necessary to rotate the spinal fixation element under the skin, the second ratchet may be rotated clockwise from an initial position to rotate the extension element and the spinal fixation element clockwise while the first ratchet is held stationary (step 962). Step 962 may be repeated as many times as necessary during the operation. The second ratchet is then retracted to the initial position, i.e. the second ratchet is rewound (step 964). If the spinal fixation element is at a target position (step 966), i.e. placed through the openings of the bone anchors and suitably placed under the skin, the spinal fixation element is disengaged from the extension element (step 968). The extension element carrying the spinal fixation element may be equipped with a decoupling mechanism for controllably decoupling the spinal fixation element from the extension element. The spinal fixation element is implanted under the skin, in the patient while the extension element is removed.

If the spinal fixation element is not at a target position, the user returns to step 960 and repeats the above discussed steps to position the spinal fixation element through the openings of the bone anchors. It may be necessary to rotate the spinal fixation element in an opposite direction, e.g. counterclockwise, for better placement (step 970). The user may then change the rotational direction of the second ratchet using the second switch provided at the proximal end of the second lever arm (step 972) and return to step 960 to repeat the above discussed steps to position the spinal fixation element. Since the rotational direction of the second ratchet is changed, counterclockwise rotation of the second ratchet rotate the spinal fixation element counterclockwise. The spinal fixation element is disengaged from the extension element once the spinal fixation element is placed in a desired position.

While the exemplary spinal fixation element rotation instrument and methods disclosed herein have been particularly shown and described with reference to minimally invasive surgeries, those of ordinary skill in the art will appreciate that the spinal fixation element rotation instrument described herein may also be used with an invasive, open surgery. When used in an open surgery, the spinal fixation element rotation instrument eliminates the need for secondary instruments to handle the spinal fixation element. The spinal fixation element rotation instrument according to the present invention will also eliminate the need to un-grip and re-grip the spinal fixation element between rotations during an open surgery. Hence, the spinal fixation element rotation instrument described herein may reduce the surgery time and reduce the required tools used during an open surgery.

The spinal fixation element rotation instrument 100 described herein may be constructed of any biocompatible material including, for example, metals, such as stainless steel or titanium, polymers, ceramics, or composites thereof. The size and diameter of elements of the spinal fixation element rotation instrument 100 may vary depending on many factors including: the type of spinal fixation element 160 and/or the type of extension element 150 used, the diameter of a surgical access port or minimally invasive incision for insertion of the spinal fixation element 160, the depth of the patient, the depth of the tissue surrounding the target location, etc. In an exemplary embodiment of the present invention, the length of the spinal fixation element rotation instrument 100 may be about 200 mm. The length of the extension element 150 may be about 150 mm. The extension element 150 may have a narrower portion that is configured to fit through the skin incision. The narrower portion of the extension element 150 may be about 60 mm. A typical skin incision fits tightly around the spinal fixation element 160 and the narrower portion of the extension element 150 that fits through the skin incision. The diameter of the narrower portion of the extension element 150 may be about 10 mm. These dimensions are for illustrative purposes only and should not be viewed as limiting. One of ordinary skill in the art will appreciate that the lever arms of the spinal fixation element rotation instrument 100 may have any dimension. However shorter lever arm will provide less mechanical advantage and thus, it will be harder to rotate the lever arm.

A person having ordinary skill in the art will appreciate that the aforementioned methods and devices for approximating bone anchors can be modified depending on the type of anchor being used, as well as the specific procedure being employed. Moreover, other methods and devices known in the art can be used in accordance with the present invention.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

While the instruments and methods disclosed herein have been particularly shown and described with reference to the exemplary embodiments thereof, those of ordinary skill in the art will understand that various changes may be made in the form and details herein without departing from the spirit and overall scope. Those of ordinary skill in the art will recognize or be able to ascertain many equivalents to the exemplary embodiments described specifically herein by using no more than routine experimentation. Such equivalents are intended to be encompassed by the overall scope and the appended claims.

The invention claimed is:

1. An instrument for rotating a spinal fixation element having a notch at a proximal end comprising:
   a first lever arm, wherein a distal end of the first lever arm is adapted to couple to the spinal fixation element; and
   a second lever arm rotatably coupled to the first lever arm at the distal end thereof, a distal end of the second lever arm being adapted to couple to the spinal fixation element, wherein the second lever arm rotates relative to the first lever arm, about a central axis of the distal ends of the first lever arm and the second lever arm to rotate the spinal fixation element from an initial position to a rotated position,
   wherein the first lever arm includes a first ratchet and the second lever arm includes a second ratchet forming a dual ratchet mechanism that prevents the spinal fixation element from rotating back toward the initial position;
   a first switch provided on a proximal end of the first lever arm, wherein the first switch allows the first ratchet to rotate clockwise when the first switch is at a first position, and the first switch allows the first ratchet to rotate counterclockwise when the first switch is at a second position;
   a second switch provided on a proximal end of the second lever arm, wherein the second switch allows the second ratchet to rotate clockwise when the second switch is at a first position, and the second switch allows the second ratchet to rotate counterclockwise when the second switch is at a second position;
   wherein a first hole is formed in the distal end of the first lever arm, and a second hole is formed at the distal end of the second lever arm, and
   an extension element having a proximal end that couples to the instrument by fitting through the first hole and the second hole, a distal end with a grabbing tip coupled to a carrier of the extension element for grabbing the spinal fixation element so that the spinal fixation element may be rotated by the instrument, a retractable sleeve surrounding the carrier, wherein in a retracted position of the retractable sleeve the grabbing tip is in an extended position and wherein in an advanced position the retractable sleeve is advanced over the carrier and the grabbing tip to prevent decoupling of the spinal fixation element from the extension element.

2. The instrument of claim 1, wherein the second lever arm comprises:
   a first section;
   a second section; and
   an attachment mechanism to attach the first section to the second section so that the first section is rotatable relative to the second section about a central axis of the attachment mechanism, wherein the central axis of the attachment mechanism is perpendicular to the central axis of the distal ends of the first lever arm and the second lever arm.

3. The instrument of claim 2, wherein the attachment mechanism is a hinge.

4. The instrument of claim 2, wherein the attachment mechanism is a loaded spring mechanism that allows the first section to assume one or more positions relative to the second section.

5. The instrument of claim 1, wherein the instrument configured to receive the spinal fixation element in a portion of an opening provided at the distal end of the first lever arm and the second lever arm.

6. The instrument of claim 1, wherein the distal ends of the first lever arm and the second lever arm are removable and replaceable.

7. The instrument of claim 1, wherein the spinal fixation element is rotated clockwise when the first ratchet and the second ratchet are set to rotate clockwise.

8. The instrument of claim 1, wherein the spinal fixation element is rotated counterclockwise when the first ratchet and the second ratchet are set to rotate counterclockwise.

9. The instrument of claim 1, wherein the first ratchet and the second ratchet lock each other out so as to prevent the spinal fixation element from rotating when the first ratchet is set to rotate in a first direction and the second ratchet is set to rotate in a second direction opposite to the first direction.

* * * * *